(12) United States Patent  
Dobson et al.

(10) Patent No.: US 8,232,102 B2
(45) Date of Patent: Jul. 31, 2012

(54) GENE DELIVERY

(75) Inventors: Jon Dobson, Stoke-on-Trent (GB); Christopher D. Batich, Gainesville, FL (US)

(73) Assignee: Nanotherics Ltd., Staffordshire (GB)

( * ) Notice: Subject to any disclaimer, the term of this patent is extended or adjusted under 35 U.S.C. 154(b) by 319 days.

(21) Appl. No.: 11/912,198

(22) PCT Filed: Apr. 21, 2006

(86) PCT No.: PCT/GB2006/001477
§ 371 (c)(1),
(2), (4) Date: Jun. 12, 2008

(87) PCT Pub. No.: WO2006/111770
PCT Pub. Date: Oct. 26, 2006

(65) Prior Publication Data
US 2008/0286361 A1    Nov. 20, 2008

(30) Foreign Application Priority Data

Apr. 22, 2005 (GB) .................................... 0508110.4

(51) Int. Cl.
*C12N 15/63* (2006.01)
*C12N 15/74* (2006.01)
*C12N 15/82* (2006.01)
*A01N 61/00* (2006.01)
*C07H 21/02* (2006.01)

(52) U.S. Cl. ....... 435/455; 435/468; 435/471; 536/23.1; 536/24.5; D13/183; 514/1; 530/350

(58) Field of Classification Search .................. 435/455, 435/468, 471; 536/23.1, 24.5; 514/1; 530/350; D13/183
See application file for complete search history.

(56) References Cited

U.S. PATENT DOCUMENTS

| 4,652,257 | A  | * | 3/1987  | Chang ............................ 604/20 |
| 6,203,487 | B1 |   | 3/2001  | Consigny |
| 2002/0193832 | A1 | * | 12/2002 | Gray |
| 2006/0228421 | A1 |   | 10/2006 | Seeney et al. |

FOREIGN PATENT DOCUMENTS

| EP | 1 482 032 A1 | 12/2004 |
| EP | 1553176 A1 | 7/2005 |
| WO | WO 02/00870 A2 * | 1/2002 |
| WO | 03/068953 A1 | 8/2003 |
| WO | 2004034876 A2 | 4/2004 |
| WO | 2005025508 A2 | 3/2005 |

OTHER PUBLICATIONS

Gersting, et al., "Gene Delivery to Respiratory Epithelial Cells by Magnetofection." The Journal of Gene Medicine. vol. 6 No. 8, pp. 913-922 (2004).
Pankhurst, et al., "Applications of Magnetic Nanoparticles in Biomedicine." Journal of Physics D: Applied Physics. vol. 36 No. 13, pp. R167-R181 (2003).
Xenariou, et al., "Magnetofection to Enhance Airway Gene Transfer." Molecular Therapy, Academic Press. vol. 9, p. 180 (2004).
Jon Dobson and Christopher D. Batich, "JPO Office Action," Japanese Patent Application No. 2008-507169, (Feb. 28, 2012).

* cited by examiner

*Primary Examiner* — Shin-Lin Chen
(74) *Attorney, Agent, or Firm* — Janet Sleath; Speckman Law Group PLLC

(57) ABSTRACT

The present invention relates to a method of delivery of a therapeutic agent to a target cell the method comprising targeting particles comprising the therapeutic agent to the cell using magnetic means to apply a magnetic force to said particles so as to tend to move said particles towards said magnetic means and at the same time moving said magnetic means.

22 Claims, 4 Drawing Sheets

A Supernatant

B No magnet

C Static magnet

D Moving magnet

GENE DELIVERY

REFERENCE TO RELATED APPLICATIONS

This application is the US national phase entry of International Patent Application No. PCT/GB2006/001477, filed Apr. 21, 2006, which claims priority to UK Patent Application No. 0508110.4, filed Apr. 22, 2005.

FIELD OF THE INVENTION

The present inventions relates to methods for the delivery of therapeutic agents to target cells.

BACKGROUND TO THE INVENTION

Cystic fibrosis causes the body to produce thick secretions that affect the lungs and digestive tract. 1 in every 10 babies born with cystic fibrosis undergoes an operation within the first few days of life due to a bowel obstruction. Children and adults suffer from repeated chest infections and problems with pancreas function. The latter complication makes it difficult for cystic fibrosis sufferers to digest food. This can lead to malnutrition, poor growth, physical weakness and delayed puberty. In older patients insulin production can become deficient due to increasing pancreatic disease thus resulting in diabetes. Cystic fibrosis can also cause blockages of liver ducts. This occurs in approximately 8% of sufferers however the health risk is so severe that liver transplants are necessary. While the disease has serious effects on the gut, pancreas, liver and reproductive tract the effect it has on the lungs are the most severe. Repeated cycles of infection lead to continuous inflammation and damage to the lungs which ultimately leads to respiratory failure and death.

Cystic fibrosis is a genetic disease caused by a mutation within a single gene, CFTR (Cystic Fibrosis Trans-membrane Conductance Regulator). Thus by treating patients using gene therapy it is possible to treat the underlying cause of the disease and not the symptoms. Introduction of CFTR has been shown to correct the cystic fibrosis defect in vitro. Gene therapy has been tested on humans using viruses and liposomes as transfection vectors. Recombinant viruses used for gene transfer need to be able to infect both dividing and non-dividing cells, integrate into the host geneome and give long term gene expression. Of all of the viral vectors tested so far (adenovirus, retrovirus, adeno-associated virus and sendai virus) non have all of these features. Viral vectors used as gene delivery systems also have potential safety issues and are ineffective long term due to a triggering of the immune response. Similar transfection problems apply to a wide variety of genetic diseases.

The present invention addresses the need for a non-viral gene transfection agent which mitigates the disadvantages associated with recombinant viral vectors. Non-viral agents are non-infectious, relatively non-immunogenic, have low toxicity, can carry larger DNA plasmids and can be produced cheaply on a large scale. One type of agent is DNA coated magnetic particles.

Current magnetic based transfection systems have a low efficiency of transformation. The present inventors have developed a magnetic particle based delivery system which has surprisingly been shown to have a transformation efficiency 10 times greater than the current systems based on initial in vitro studies.

BRIEF SUMMARY OF THE DISCLOSURE

According to a first aspect of the invention there is provided a method of delivery of a therapeutic agent to a target cell the method comprising targeting particles comprising the therapeutic agent to the cell using magnetic means to apply a magnetic force to the particles so as to tend to move the particles towards or away from the magnetic means and at the same time moving the magnetic means.

In a preferred aspect of the invention the magnetic means are used to apply a magnetic force to the particles so as to tend to move the particles in a first direction towards or away from the magnetic means and at the same time moving the magnetic means relative to the particles in a second direction at an angle to the first direction.

The movement of the magnetic means in a second direction is generally at a non-zero angle to the first direction, for example at an angle between 0 and 180°, such as at an angle of between 0 and 90°, to the first direction.

Preferably the movement of the magnetic means in a second direction is an oscillating movement. The oscillation frequency at which the magnet(s) is driven will usually be varied and will generally be in the range of 0 up to 100 Hz although values outside this range may be used.

In a preferred aspect of the invention the movement of the magnetic means in a second direction is substantially perpendicular to the first direction in which the particles tend to move.

The magnetic force applied to the particles so as to move the particles towards or away from the magnetic means may be described as a translational force. The translational force is produced by a magnetic field with a gradient. Preferably the direction of the translational force is towards the magnet.

In a preferred aspect of the invention the magnetic means is a magnet or array of magnets. The magnet may be an electromagnet.

The particles may be attracted to, or repelled from, the magnetic means. Preferably the particles are attracted to the magnetic means.

In a further preferred aspect of the invention the particle is a magnetic particle. Preferably the particle is made from a magnetisable material. The magnetisable particle may be inherently magnetic or may be one which reacts in a magnetic field.

Generally, any magnetic material may be used, however, by the term magnetic we mean, for example, a material which is paramagnetic superparamagnetic, ferromagnetic, and/or antiferromagnetic, examples of which include elemental iron, chromium manganese, cobalt, nickel, or a compound thereof. The iron compound may be an iron salt which may be selected from the group which includes magnetite ($Fe_3O_4$), maghemite ($\gamma Fe_2O_3$) and greigite ($Fe_3S_4$), or any combination thereof. The chromium compound may be chromium dioxide.

The particles may be provided within the pores of a polymer. Alternatively, the particles may comprise a magnetic core with a biocompatible coating. The biocompatible coating may comprise a polymer, e.g dextran, polyvinyl alcohol (PVA), polyethylenimine (PEI) or silica.

In a further preferred aspect of the invention the particles have a mean size of between 10 µm and 5 nm, for example between 1 µm and 10 nm.

Preferably the particles are nanoparticles.

Larger, magnetically blocked particles (>30 nm for magnetite) will experience a torque in the oscillating field as the field vector changes its angle with respect to the magnetisation vector of the particles according to the equation:

$$\tau = \mu B \sin \theta$$

where $\tau$ is the torque, $\mu$ is the magnetic moment, B is the magnetic flux density and $\theta$ is the angle between the applied field and the particle's magnetisation vector. This twisting, wedging and pulling enhances the movement of the particle/therapeutic agent complex resulting in the improved uptake in the cells.

In the method of the invention the cell may be a bacterial cell, plant cell or animal cell. The animal cell may be a mammalian cell for example a human cell.

In the method of the invention the cell may be a lung cell, kidney cell, nerve cell, mesenchymal cell, muscle cell (cardiomyocyte), liver cell, red or white blood cell (eg erythrocyte, lymphocyte, monocyte, macrophage, leukocyte), pancreatic p cell; epithelial cell (eg lung, gastric), endothelial cell, bone cell, skin cell, gastrointestinal cell, bladder cell, reproductive cell (sperm or egg cell), cells of the uterus, prostate or endocrine gland (e.g pituitary); embryonic stem (ES) cells; embryonal germ (EG) cells, tumour cell, cancer cell.

The method of the invention may be an ex vivo or in vivo method. Preferably the method is carried out in vivo.

The method described herein has application in the treatment of a wide range of disorders including. Thus the method has application as a method for the treatment or prevention of clinical disorders and diseases.

In the method of the invention the therapeutic agent may be a pharmaceutical, nutraceutical or agrochemical agent. The pharmaceutical agent may include DNA, RNA, interfering RNA (RNAi), a peptide, polypeptide, an antibody (e.g antibody fragment such as a single chain antibody fragment), an aptamer, a small molecule. Small molecules may include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

In a preferred method of the invention the therapeutic agent is DNA. In a further preferred method of the invention, the therapeutic agent is the gene encoding the Cystic Fibrosis Trans-membrane Conductance Regulator.

A further aspect of the invention provides the use of moveable magnetic means in the manufacture of a system for targeting particles comprising a therapeutic agent to a target cell. Preferably the magnetic means are in motion, preferably still in constant motion.

In a preferred use according to the invention the magnetic means are used to apply a magnetic force to the particles so as to tend to move the particles towards or away from the magnetic means and at the same time moving the magnetic means.

In a further preferred use according to the invention the magnetic means are used to apply a magnetic force to the particles so as to tend to move the particles in a first direction towards or away from the magnetic means and at the same time moving the magnetic means relative to the particles in a second direction at an angle to the first direction.

Where the use is in vivo, the magnetic means may be moved external to the body. The movement of the magnetic means may be controlled by a motor or a magnet. The movement of the magnetic means may be remotely controlled.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention will be described by way of example only with reference to the following figures:

EXAMPLE

The reporter genes, Green Fluorescent Protein (GFP) and luciferase, were attached to commercially available magnetic nanoparticles. The particles generally consisted of a magnetic core (magnetite—$Fe_3O_4$ and/or its oxidation product maghemite—$gFe_2O_3$) with a polymer coating, such as dextran, PVA or silica, and ranged in size from ~10 nm to ~1 µm. Magnetite is a naturally occurring iron oxide and is found in many organs in the human body. In addition magnetite is FDA-approved for MRI contrast enhancement and thus is suitable for clinical trials.

Magnetic nano-particles coated with 1800 branched polyethyleneimine (PEI) were incubated with DNA in order to bind the reporter genes to the particles. The gene/particle complex was then introduced into mono-layer cultures of HEK293T kidney cells within the incubator. Culture dishes were positioned on a custom-built holder above the magnet array, housed within the incubator.

The reporter gene/particle complex is targeted to cells via a high gradient rare earth (NdFeb) magnet which are focused over the target site. These magnets produce a translational force on the particles due to the high field strength/gradient product according to the equation:

$$F_{mag} = (x_2 - x_1)V\frac{1}{\mu_o}B(\nabla B)$$

where $x_2$ is the volume magnetic susceptibility of the magnetic particle, $x_1$ is the volume magnetic susceptibility of the surrounding medium, $\mu_o$ is the magnetic permeability of free space, B is the magnetic flux density in Telsa(T) (Pankhurst el al. 2003). This translational force 'pulls' the particles towards the magnet.

The particles are delivered using a high precision oscillating horizontal drive system is controlled by a computer and custom designed control software, designed by Jon Dobson. The amplitude of the array's drive system can vary between a few nanometers to millimetres and the frequency can vary from static up to 100's of Hz depending upon the parameters for the target.

HEK293T cells were seeded in 96 well plates at $5\times10^3$ cells/well. The cells were transfected with 5 ug/well of 150 nm dextran/magnetite composite nanoparticles coated with PEI, loaded with pCIKlux DNA (binding capacity approx 0.2 ug DNA/ug particles). The cells were exposed to magnetic fields as shown for 24 hr post transfection, using a stack of 3×NdFeB 4 mm magnets per well. The cells exposed to moving field were exposed for 2 hrs at 2 Hz using a 200 μm displacement and then the magnets left in place for 22 hrs in static position.

Figure 1:
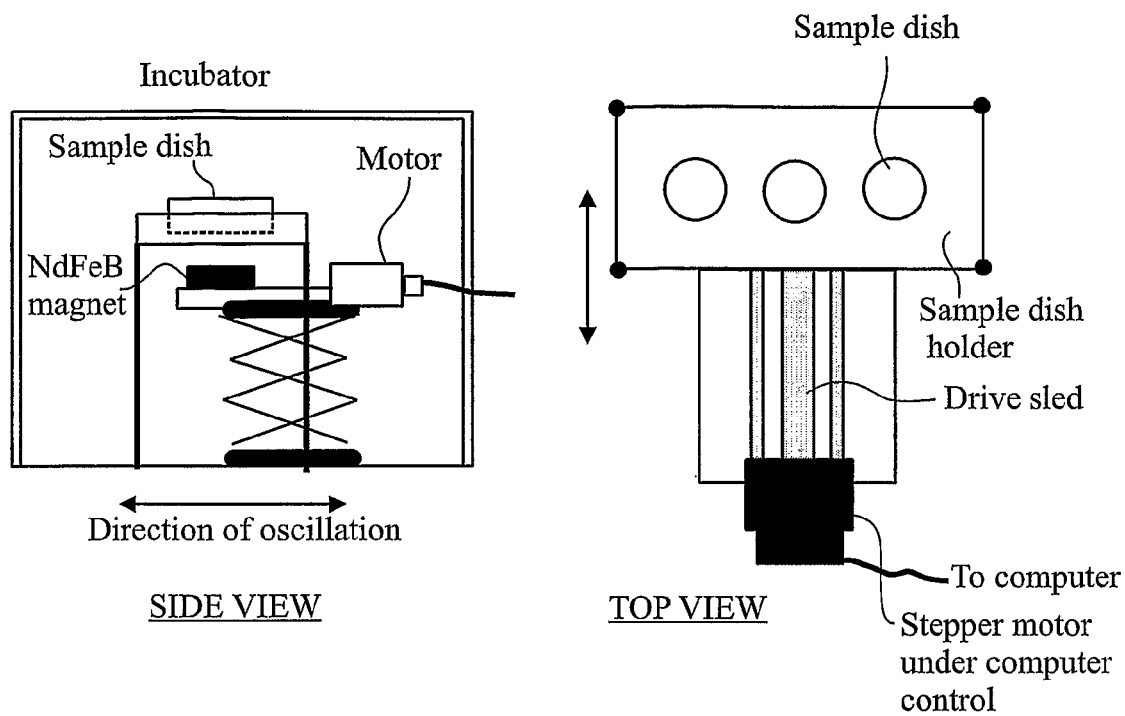
FIG. 1 is a schematic representation of the magnet array drive system and sample holder for in vitro cell culture and Air/Liquid Interface (tissue) studies.
Figure 2:
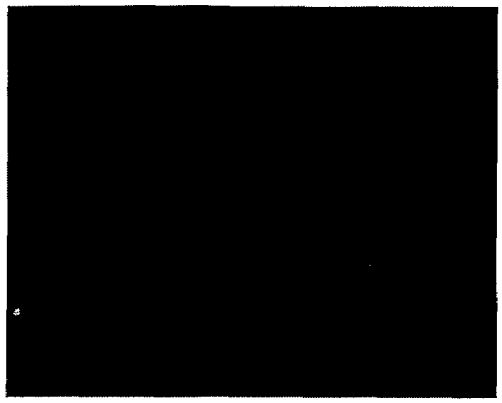
FIG. 2 shows GFP expression in HEK293T cells transfected with 150 nm magnetic nanoparticles coated with pEG-FPC1 DNA in response to magnetic field.
Figure 2:
Figure 2:
Figure 2:
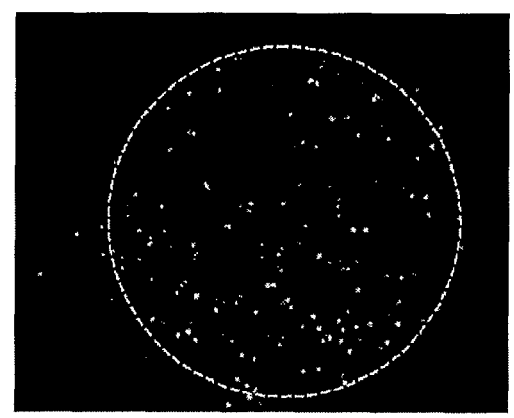
Figure 3:
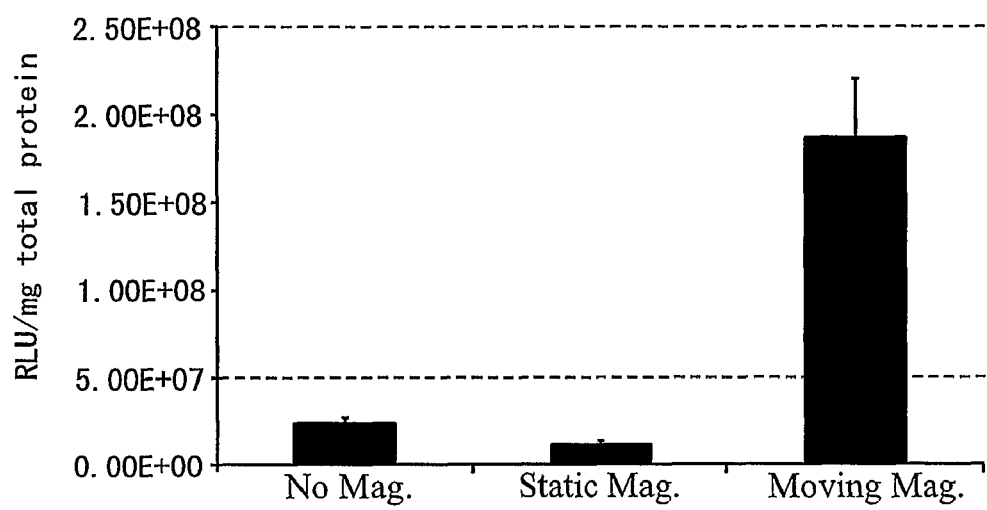
FIG. 3 is a histogram showing luciferase activity in HEK293 T cells transfected with 150 nm magnetic nanoparticles coated with pCIKLux luciferase reporter.
Figure 4:
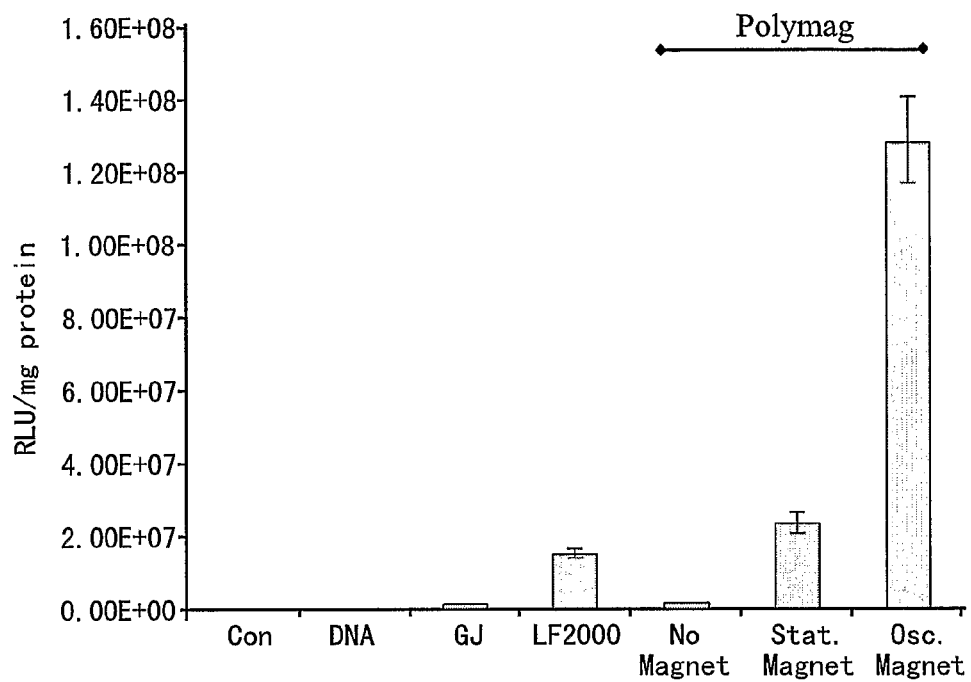
FIG. 4 is a histogram showing luciferase activity in NCI-H292 human lung epithelial cells transfected with OzBiosciences Polymag® particles coated with pCIKLux luciferase reporter construct in response to static and oscillating magnetic fields. All transfections were performed in 96 well tissue culture plates using 0.1 µg DNA/well. Genejuice (GJ) and Lipofectamine 2000 (LF2000) transfections were carried out according to the manufacturer's recommended protocol. Data shown as mean ±SEM (n=6 for all groups). Magnet diameter=6 mm.

Data shown in FIGS. 2 and 3 as average +/−SEM (n=12 for each group).

The invention claimed is:

1. An in vitro method of delivery of an agent into a target cell, the method comprising: positioning a layer of target cells above a magnetic means, wherein said magnetic means is a magnet or array of magnets; introducing magnetic particles comprising the agent to the cells; and using said magnetic means to apply a magnetic force to said magnetic particles so as to move said magnetic particles towards said magnetic means and towards the cells, and at the same time oscillating said magnetic means, wherein the direction of oscillation of said magnetic means is substantially perpendicular to the direction of attraction of the magnetic particles toward said magnetic means, and wherein the magnetic force applied to said magnetic particles is a translational force, whereby the agent is delivered into the target cell.

2. The method of claim 1 wherein said magnet is an electromagnet.

3. The method of claim 1 wherein the magnetic particle is made from a magnetisable material.

4. The method of claim 1 wherein the magnetic particle is made from a magnetisable material selected from the group consisting of: elemental iron, chromium, manganese, cobalt, nickel, and compounds thereof.

5. The method of claim 4 wherein the iron compound is an iron salt.

6. The method of claim 5 wherein the iron salt is selected from the group consisting of: magnetite ($Fe_3O_4$), maghemite ($\gamma Fe_2O_3$), greigite ($Fe_3S_4$), and combinations thereof.

7. The method of claim 1 wherein the magnetic particles have a mean size of between 10 μm and 5nm.

8. The method of claim 7 wherein the magnetic particles have a mean size between 1 μm and 5 nm.

9. The method of claim 1 wherein the magnetic particles are nanoparticles.

10. The method of claim 1 wherein the cell is a bacterial cell.

11. The method of claim 1 wherein the cell is a plant cell.

12. The method of claim 1 wherein the cell is an animal cell.

13. The method of claim 12 wherein the cell is a mammalian cell.

14. The method of claim 13 wherein the cell is a human cell.

15. The method of claim 1 wherein the cell is a lung cell, kidney cell, nerve cell, mesenchymal cell, muscle cell (cardiomyocyte), liver cell, red or white blood cell, erythrocyte, lymphocyte, monocyte, macrophage, leukocyte, pancreatic β cell; epithelial cell, endothelial cell, bone cell, skin cell, gastrointestinal cell, bladder cell, reproductive cell, sperm cell, egg cell, a cell of the uterus, prostate or endocrine gland, pituitary cell; embryonic stem (ES) cell; embryonal germ (EG) cell, tumor cell, or cancer cell.

16. The method of claim 1 wherein the agent is a therapeutic agent.

17. The method of claim 1 wherein the agent is DNA, RNA, interfering RNA (RNAi), a peptide, polypeptide, an antibody, a single chain antibody fragment, an aptamer, or a small molecule.

18. The method of claim 17 wherein the agent is DNA.

19. The method of claim 1, wherein the magnetic means oscillates with a frequency in the range of 1 to 100 Hz.

20. The method of claim 1, wherein the amplitude of oscillation of the magnetic means is in the nanometer to millimeter range.

21. The method of claim 1, wherein the agent is a polynucleotide, RNA or DNA and the method is a method of genetic transformation of the target cell.

22. The method of claim 1, wherein oscillating said magnetic means in the direction substantially perpendicular to the direction of attraction of the magnetic particles toward said magnetic means increases transformation efficiency.

* * * * *